United States Patent
Florio et al.

(10) Patent No.: US 7,006,868 B2
(45) Date of Patent: Feb. 28, 2006

(54) METHOD AND APPARATUS FOR USING A REST MODE INDICATOR TO AUTOMATICALLY ADJUST CONTROL PARAMETERS OF AN IMPLANTABLE CARDIAC STIMULATION DEVICE

(75) Inventors: Joseph J. Florio, La Canada, CA (US); Gene A. Bornzin, Simi Valley, CA (US); Peter Boileau, Valencia, CA (US); Eric Falkenberg, Simi Valley, CA (US); Janice Barstad, Eden Prairie, MN (US)

(73) Assignee: Pacesetter, Inc., Sylmar, CA (US)

( * ) Notice: Subject to any disclaimer, the term of this patent is extended or adjusted under 35 U.S.C. 154(b) by 631 days.

(21) Appl. No.: 10/092,695

(22) Filed: Mar. 6, 2002

(65) Prior Publication Data

US 2003/0171781 A1 Sep. 11, 2003

(51) Int. Cl.
*A61N 1/365* (2006.01)

(52) U.S. Cl. ...................................................... 607/19
(58) Field of Classification Search ................ 607/2–9, 607/14, 19, 39–41, 118, 123
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,940,052 A | 7/1990 | Mann et al. | 128/419 G |
| 4,944,298 A | 7/1990 | Sholder | 128/419 G |
| 5,203,326 A * | 4/1993 | Collins | 607/4 |
| 5,330,507 A * | 7/1994 | Schwartz | 607/14 |
| 5,466,254 A | 11/1995 | Helland | 607/123 |
| 5,476,483 A | 12/1995 | Bornzin et al. | 607/17 |
| 5,733,312 A | 3/1998 | Schloss et al. | 607/17 |
| 5,874,420 A | 2/1999 | Pelleg | 514/81 |
| 5,891,176 A | 4/1999 | Bornzin | 607/18 |
| 6,049,734 A | 4/2000 | Lang | 607/9 |
| 6,058,328 A | 5/2000 | Levine et al. | 607/14 |
| 6,115,627 A | 9/2000 | Street | 600/515 |
| 6,216,037 B1 | 4/2001 | Van Oort | 607/28 |
| 6,249,702 B1 | 6/2001 | Van Oort | 607/11 |

FOREIGN PATENT DOCUMENTS

WO     WO 01/76686 A2     4/2001

* cited by examiner

*Primary Examiner*—George Manuel

(57) ABSTRACT

An implantable cardiac stimulation device is described wherein a controller of the cardiac stimulation device controls selected functions of the device based on whether the patient is at rest and further based on whether the patient is prone to vagally-mediated arrhythmias. Functions of the device that may be controlled include, for example, a pacing base rate, an AV/PV delay, and a refractory period as well as overdrive pacing parameters and diagnostic data gathering parameters. In one example, if the patient is not prone to vagally-mediated arrhythmias, the base rate is lowered while the patient is at rest. Also, overdrive pacing parameters are set to be less aggressive. As such, the operation of the cardiac stimulation device is controlled to make it easier for the patient to rest while also reducing power consumption. However, if the patient is prone to vagally-mediated arrhythmias, the base rate is not lowered while the patient is at rest. Overdrive pacing parameters are instead set to be more aggressive, rather than less aggressive. In this manner, the cardiac stimulation device attempts to compensate for any increased risk of arrhythmia that may occur while the patient, who is prone to vagally-mediated arrhythmias, is at rest. Numerous other parameters may be adjusted dependent upon whether the patient is at rest or dependent upon whether the patient is prone to vagally-mediated arrhythmias.

21 Claims, 6 Drawing Sheets

METHOD AND APPARATUS FOR USING A REST MODE INDICATOR TO AUTOMATICALLY ADJUST CONTROL PARAMETERS OF AN IMPLANTABLE CARDIAC STIMULATION DEVICE

CROSS-REFERENCE TO RELATED APPLICATIONS

This application is related to copending U.S. patent application Ser. No. 10/093,225 filed Mar. 6, 2002, titled "Method and Apparatus for Using a Rest Mode Indicator to Automatically Adjust Control Parameters of an Implantable Cardiac Stimulation Device."

FIELD OF THE INVENTION

The invention generally relates to implantable cardiac stimulation devices such as pacemakers or implantable cardioverter-defibrillators (ICDs) and in particular to techniques for controlling operation of such devices.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Another example is a tachycardia wherein the heart beats at an abnormally fast rate. With atrial tachycardia, the atria of the heart beat abnormally fast. With ventricular tachycardia, the ventricles of the heart beat abnormally fast. Though often unpleasant for the patient, a tachycardia is typically not fatal. However, atrial tachycardia can trigger atrial fibrillation (AF) wherein the atria of the heart beat chaotically reducing the efficiency by which blood is pumped from the heart. Ventricular tachycardia can trigger ventricular fibrillation (VF) wherein the ventricles of the heart beat chaotically resulting in little or no net flow of blood from the heart to the brain and other organs. If not terminated, VF is fatal. Death resulting from VF represents one type of sudden cardiac death (SCD). Hence, it is highly desirable to prevent or terminate arrhythmias, particularly arrhythmias of the type that may lead to VF.

A variety of implantable cardiac stimulation devices have been developed to monitor the heart to detect arrhythmias and to administer appropriate therapy. Pacemakers are implantable devices programmed to recognize certain arrhythmias such bradycardia or tachycardia and to deliver low-voltage electrical pacing pulses to the heart using various pacing leads implanted within the heart in an effort to remedy the arrhythmia. For bradycardia, for example, the pacemaker may be programmed to pace the heart whenever the natural or "intrinsic" heart rate falls below a programmed base rate, thereby preventing abnormally slow heart rates. A determination of when to deliver individual pacing pulses is typically made using various routine programmable parameters such as AV/PV delay and refractory period.

Some pacemakers are also programmed to overdrive pace the heart above the base rate in an attempt to prevent a tachycardia from occurring, and thereby help prevent AF or VF from being triggered. Briefly, with overdrive pacing, the cardiac stimulation device paces the heart so that most beats are paced beats rather than intrinsic beats. To this end, the device occasionally determines the intrinsic heart rate of the patient from a pair of intrinsic beats and then paces the heart at a rate typically five or ten beats per minute (bpm) faster than the intrinsic rate. Thus, if the intrinsic rate exceeds the base rate, the heart will be paced at a still higher overdrive rate. If the intrinsic rate falls below the base rate, the heart usually will be paced at the base rate. In either case, most resulting beats are paced beats rather than intrinsic beats. Typically, the base rate and overdrive rate are programmed by the physician so as to achieve a high degree of overdrive pacing, as represented by the percentage of paced beats out of total beats. In many patients, overdrive pacing helps prevent a tachycardia from occurring and, if a tachycardia nevertheless occurs, overdrive pacing at a still higher rate than the tachycardia can help terminate the tachycardia and reduce the risk that the tachycardia might trigger a fibrillation, either AF or VF.

Pacemakers, however, are usually not capable of terminating AF or VF if such as fibrillation nevertheless occurs. High-voltage electrical shocks typically must be delivered to the heart to terminate fibrillation. Hence, patients prone to AF or VF are usually provided with an ICD, which is an implantable cardiac stimulation device capable of delivering the necessary high-voltage electrical shocks to the heart when AF or VF occurs. The ICD includes a set of defibrillation capacitors for storing charge. In use, when it appears that a defibrillation pulse may need to be delivered, the ICD charges the capacitors to high voltage levels and then, if a pulse is indeed necessary, the ICD delivers pulse to the heart of the patient. ICDs may also be configured to perform routine pacing functions, such as base rate pacing or overdrive pacing. Both pacemakers and ICDs typically gather and record a substantial amount of diagnostic data pertaining to the patient and to the device itself. Diagnostic data pertaining to the patient may include internal electrocardiograms (IEGMs) and the detection of such events as premature atrial contractions (PACs) or premature ventricular contractions (PVCs). Diagnostic data pertaining to the patient may include the impedance of the leads used for pacing and the voltage of the power supply of the device.

Some state-of-the-art implantable cardiac stimulation devices are programmed to detect when the patient is in a state of profound rest (such as sleep) and to reduce the base pacing rate while the patient is at rest. This often makes it easier for the patient to sleep and also conserves battery resources within the pacemaker. To this end, the pacemaker may be provided with an activity sensor, which detects the amount of physical activity of the patient. If the activity level is very low for a predetermined period of time, a determination is thereby made that the patient is at rest and the device switches to a rest mode wherein the base rate is lowered.

Although the detection of whether the patient is at rest has been advantageously used to lower the pacing base rate, it does not appear that any state-of-the-art cardiac stimulation devices have used rest detection for use in adjusting other functions of the device. It may be beneficial to also adjust other pacing parameters such as overdrive pacing parameters to, for example, lower overdrive pacing rates while the patient is at rest make it even easier for the patient to sleep and to further conserve battery power. It may also be beneficial to adjust diagnostic-gathering parameters of the device based on whether the patient is at rest, such as the specific types of data to be gathered or how frequently the data is to be gathered, also to further conserve power when possible. In general, many control parameters of an implantable cardiac stimulation device can be adjusted based on rest detection to achieve various advantages.

Accordingly, aspects of the invention are directed to providing improved techniques for exploiting the determination of whether a patients is at rest.

Within some patients, arrhythmias may be vagally-mediated, i.e. decreased vagal tone can trigger the arrhythmia. Vagal tone relates to a basal level of activity in the body maintained by the vagus nerve. The vagus nerve, which is a portion of the parasympathetic nervous system, regulates the function of various organs and tissues including the heart by sending neural signals to the organs through efferent vagal fibers. The neural signals provided by the vagus nerve serve to maintain the basal level of activity within the body. Vagal tone is automatically increased or decreased by the parasympathetic nervous system in response to internal or external sensory stimuli depending upon the needs of the body. For example, when the patient is asleep, the parasympathetic nervous system decreases the vagal tone of the body, making various organs less active and, in particular, lowering the heart rate. The lower heart rate can result in PACs or PVCs, which, in turn, can trigger tachyarrhythmias, including VF. As a result, some patients prone to vagally-mediated arrhythmias are much more likely to suffer SCD while asleep, then while awake.

Thus, for patients prone to vagally-mediated arrhythmias, any lowering of the base rate during sleep during sleep can significantly increase the risk of arrhythmias, such as bradycardias and tachycardias, occurring during sleep. However, heretofore, pacemakers and ICDs have been programmed to administer therapy without regard to whether the patient is prone to vagally-mediated arrhythmias. Hence, the devices do not compensate for the higher risk within patients prone to vagally-mediated arrhythmias while the patients are asleep. Indeed, as noted, many pacemakers and ICDs actually lower the base rate while the patient is asleep and thereby possibly increase the risk of an arrhythmia within the patient. For patients prone to vagally-mediated arrhythmias, it may be preferable to instead increase the base rate while the patient is asleep. It may also be preferable to increase an "aggressiveness" of overdrive pacing while the patient is asleep so as to achieve a higher degree of overdrive pacing while the patient is at greater risk of a tachycardia.

Accordingly, aspects of the invention are also directed to providing improved techniques for controlling implantable cardiac stimulation devices for use in patients prone to vagally-mediated arrhythmias. In particular, aspects are directed to an improved control technique for use with patients prone to vagally-mediated arrhythmias that takes into account whether the patient is at rest and adjusts pacing parameters accordingly.

SUMMARY OF THE INVENTION

In accordance with one aspect of the invention, a system and method are provided for use within an implantable cardiac stimulation device for implant within a patient wherein a controller of the cardiac stimulation device controls selected functions of the device based on whether the patient is at rest and whether the patient is prone to rest-related physiologic problems. In accordance with the method, a determination is made as to whether the patient is at rest. Then, selected functions of the cardiac stimulation device are controlled using a first set of control parameters if the patient is at rest and a second set of control parameters if the patient is not at rest. The sets of control parameters specify one or more of AV/PV delay, refractory period, overdrive pacing parameters, diagnostic-data gathering parameters and defibrillation capacitor charging parameters.

The set of control parameters may further specify a base pacing rate for use while the patient is at rest and different base pacing rate for use otherwise. In this manner, the many functions of the device may be advantageously controlled based on whether the patient is at rest to, for example, optimize the operation of the device while the patient is at rest.

In accordance with another aspect of the invention, a system and method are provided for use within an implantable cardiac stimulation device for implant within a patient wherein a controller of the cardiac stimulation device controls selected functions of the device based on whether the patient is prone to vagally-mediated arrhythmias or other rest-related physiologic problems. In this manner, the many functions of the device may be advantageously controlled based on whether the patient is prone to vagally-mediated arrhythmias to, for example, optimize the operation of the device for use with patients prone to vagally-mediated arrhythmias.

In accordance with other aspects of the invention, systems and methods are provided for use within implantable cardiac stimulation devices wherein the controller of the device controls selected functions of the device based on whether the patient is at rest and also whether the patient is prone to vagally-mediated arrhythmias.

In an exemplary embodiment, wherein functions are controlled both based on whether the patient is at rest and whether the patient is prone to vagally-mediated arrhythmias, the implantable cardiac stimulation device receives various sets of control parameters from an external programmer including "normal rest-mode" control parameters for use with patients not prone to vagally-mediated arrhythmias, "VMA rest-mode" control parameters for use with patients prone to vagally-mediated arrhythmias, and "non-rest-mode" control parameters for use while the patient is not at rest. The specific control parameters of the various sets of control parameters are selected by a physician or other medical professional programming the device. The external programmer also sends a control signal to the cardiac stimulation device indicating whether, in the opinion of the physician programming the device, the patient is prone to vagally-mediated arrhythmias. Thereafter, the device periodically determines whether the patient is at rest using an activity sensor, if the patient is not at rest, the "non-rest-mode" control parameters are used to control the operation of the device, if the patient is at rest and is prone to vagally-mediated arrhythmias, the "VMA rest-mode" control parameters are instead used to control the operation of the device. If the patient is at rest but is not prone to vagally-mediated arrhythmias, the "normal rest-mode" control parameters are instead used to control the operation of the device.

In one specific example, the "normal rest-mode" set of control parameters are selected such that, while the patient is at rest, the base rate is lowered, overdrive pacing is less aggressive, and diagnostic information is recorded less frequently. Hence, for patients not prone to vagally-mediated arrhythmias, the cardiac stimulation device is controlled to make it easier for the patient to rest and to reduce power consumption while the patient is at rest. However, the "VMA rest-mode" set of control parameters are selected such that, while the patient is at rest, the base rate is not lowered, overdrive pacing is more aggressive, and diagnostic information is recorded more frequently. Hence, for patients prone to vagally-mediated arrhythmias, the cardiac stimulation device is controlled so as to compensate for the greater risk of arrhythmia occurring while the patient is asleep and to record a greater amount of data to aid the physician during a subsequent follow-up session in diagnosing any arrhythmias that nevertheless occurred while the patient was asleep. The "VMA rest-mode" control parameters may also specify that the defibrillation capacitors are to be automatically charged whenever the patient falls asleep so that, if fibrillation occurs, a defibrillation pulse can immediately be delivered to the heart of the patient.

Numerous other parameters may be adjusted dependent upon whether the patient is at rest and/or dependent upon whether the patient is prone to vagally-mediated arrhythmias. The other parameters and other general objects, features and advantages of the invention are discussed below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
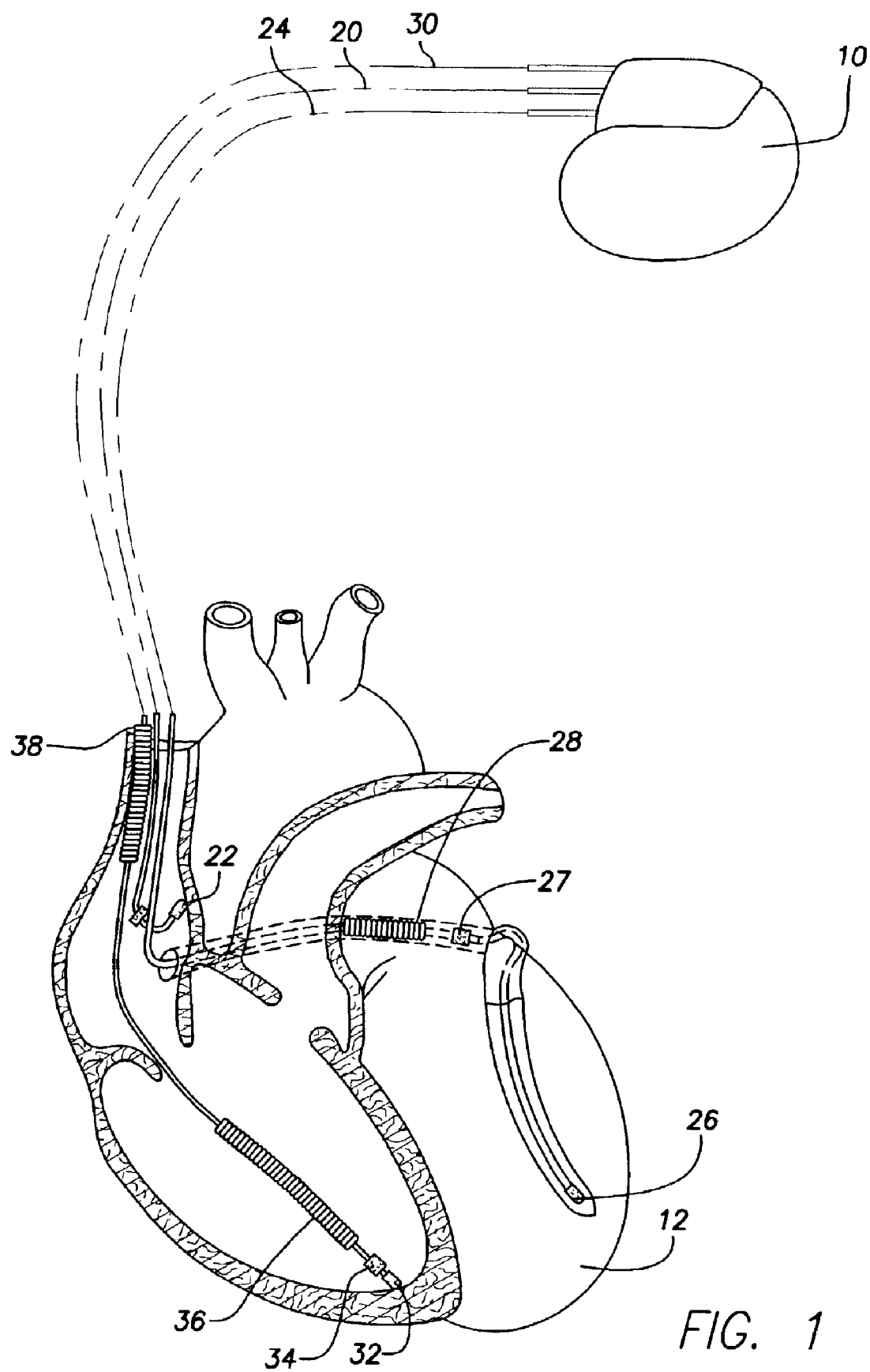
FIG. 1 is a simplified diagram illustrating an implantable cardiac stimulation device in electrical communication with at least three leads implanted into the heart of a patient for delivering multi-chamber stimulation and shock therapy and configured in accordance with the invention.

As shown in FIG. 1, there is a cardiac stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the cardiac stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the cardiac stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which patents are hereby incorporated herein by reference.

The cardiac stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
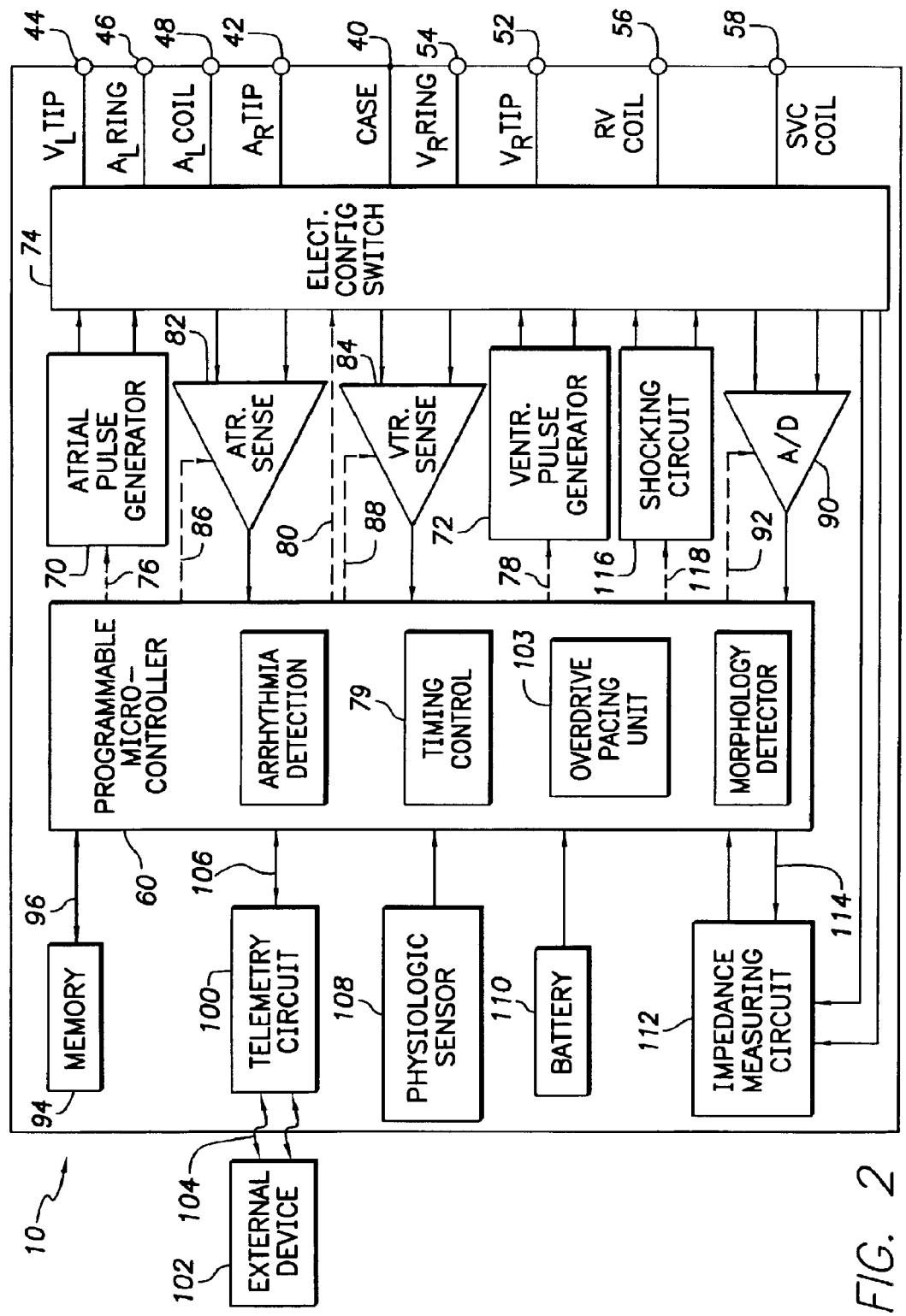
FIG. 2 is a functional block diagram of the implantable cardiac stimulation device of FIG. 1 illustrating basic elements of the cardiac stimulation device.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the cardiac stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the cardiac stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. No. 4,712,555 (Sholder) and U.S. Pat. No. 4,944,298 (Sholder).

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the cardiac stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate. As will be described more fully below, different sets of control parameters are stored for use depending upon whether the patient is in a state of profound rest and whether the patient is prone to vagally-mediated arrhythmias.

The microcontroller includes an overdrive pacing unit 103 for controlling overdrive pacing based on a set of additional control parameters including an overdrive pacing response function, a number of overdrive events; and a recovery rate. The overdrive pacing response function specifies the overdrive pacing rate to be applied when overdrive pacing is triggered. Overdrive pacing is triggered upon the detection of X intrinsic heart beats within a "window" of Y paced or intrinsic beats. In a particular example, overdrive pacing is triggered if two of the last sixteen beats were intrinsic. The number of overdrive events specifies the number of consecutive beats to be paced following triggering of a sequence of overdrive pacing beats. The recovery rate specifies a rate decrement by which the overdrive pacing rate is to be decreased after the number of overdrive events have been paced.

In use, overdrive pacing unit 103 monitors heart beats of the patient and, if two intrinsic heart beats out of sixteen paced or intrinsic beats are detected, overdrive pacing is triggered. The overdrive pacing rate is determined using the overdrive pacing response function and the heart rate at the time overdrive is triggered. Overdrive pacing unit 103 overdrive paces the heart at the selected overdrive pacing rate for a programmed number of overdrive events. Thereafter, overdrive pacing unit 103 slowly decreases the overdrive pacing rate by a rate decrement specified by the programmed recovery rate. If during delivery of the number of paced overdrive events or if during the rate recovery two intrinsic heart beats out of sixteen paced or intrinsic beats are again detected, then the overdrive pacing unit repeats the process to determine a new overdrive pacing rate and paces accordingly. If a base rate is programmed, such as 60 bpm, the heart will be paced at the base rate even if the recovery rate would otherwise cause the rate to decrease even further.

It is believed that overdrive pacing is effective for at least some patients for preventing or terminating the onset of tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods which, in turn, can trigger a tachycardia. By overdrive pacing the heart at a uniform rate, the likelihood of the occurrence of ectopic pulses is reduced and the refractory periods within the heart tissue are thereby rendered more uniform and periodic. Thus, the dispersion of refractory periods is reduced and tachycardias are substantially avoided. If a tachycardia nevertheless occurs, overdrive pacing at a rate faster than a tachycardia helps to eliminate any ectopic pulses that may be occurring and thereby helps terminate the tachycardia.

Figure 3:
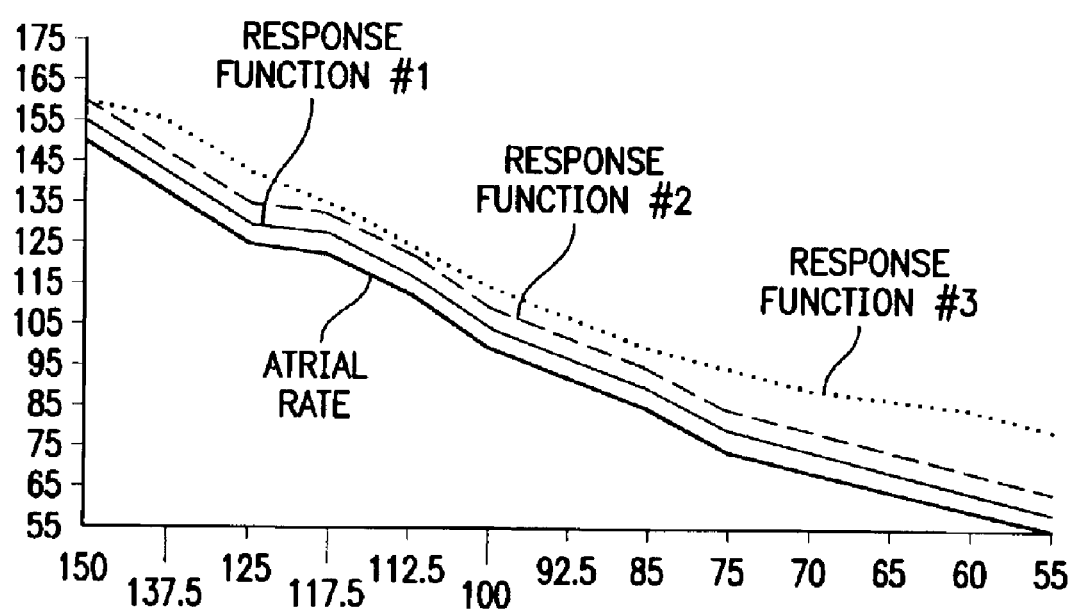
FIG. 3 is a graph illustrating overdrive pacing response functions for use by the device of FIG. 2 while performing overdrive pacing.

With regard to the overdrive pacing response functions, typically one or more overdrive pacing response functions is pre-programmed into the cardiac stimulation device. Each specifies an overdrive pacing rate for each corresponding intrinsic heart rate throughout a broad range of detectable heart rates, such as from 55 bpm to 150 bpm. FIG. 3 illustrates an exemplary set of three response functions or slopes each of which specifies an overdrive pacing rate (shown on the y-axis) as a function of the intrinsic atrial rate (shown on the x-axis). The intrinsic atrial is rate is shown in bold. Briefly, the cardiac stimulation device is programmed to select one of the response functions. While overdrive pacing is enabled, the cardiac stimulation device detects the intrinsic heart rate then determines the overdrive pacing rate corresponding to the intrinsic rate by examining the selected response function then paces the heart at that rate. If response function #1 has been selected and the intrinsic rate is 70 bpm, an overdrive pacing rate of 75 ppm is specified by the response function and the heart is overdrive paced at that rate. If response function #2 has been selected and the intrinsic rate is 70 bpm, an overdrive pacing rate of 80 ppm and the heart is overdrive paced at that rate. The higher the overdrive rate as compared to the intrinsic rate, the more aggressive the overdrive pacing. By providing multiple response functions, the aggressiveness of overdrive pacing can be adjusted. (Typically, a half dozen or more response functions are provided. For clarity in illustrating the response functions, only three are shown in the figure.)

Other techniques for reducing the likelihood of arrhythmias that may be performed by the controller are described in U.S. Pat. No. 6,058,328 (Levine et al.), issued May 2, 2000, which patent is hereby incorporated by reference. The other techniques may be used in addition to or in the alternative to the overdrive pacing technique described above.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the cardiac stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. The type of sensor used is not critical to the invention and is shown only for completeness.

In the preferred embodiment, the cardiac stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the cardiac stimulation device 10, it is to be understood that the physiologic sensor 108 may also be external to the cardiac stimulation device 10, yet still be implanted within or carried by the patient. A common type of rate responsive sensor is an activity sensor, such as an accelerometer or a piezoelectric crystal, which is mounted within the housing 40 of the cardiac stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The invention utilizes a "sleep state" or diurnal sensor that can detect sleep and wake states. One such sensor is known as "activity variance" wherein an activity sensor is monitored diurnally to detect the low variance in the measurement corresponding to the sleep state. For a complete description of the activity variance sensor, see U.S. Pat. No. 5,476,483 (Bornzin et al.), issued Dec. 19, 1995, which patent is hereby incorporated by reference.

The cardiac stimulation device additionally includes a battery 110 which provides operating power to all of the circuits shown in FIG. 2. For the cardiac stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the cardiac stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With reference to the remaining figures, various embodiments of the control parameter adjustment techniques of the invention will be described. In a first embodiment, described with reference to FIG. 4, the microcontroller of the cardiac stimulation device operates based on control parameters selected depending upon whether the patient is at rest. In a second embodiment, described primarily with reference to FIG. 5, the control parameters are further selected based on whether the patient is prone to vagally-mediated arrhythmias. In a third embodiment, described primarily with reference to FIG. 6, a rest-mode threshold for determining whether the patient is at rest is set based on whether the patient is prone to vagally-mediated arrhythmias.

Figure 4:
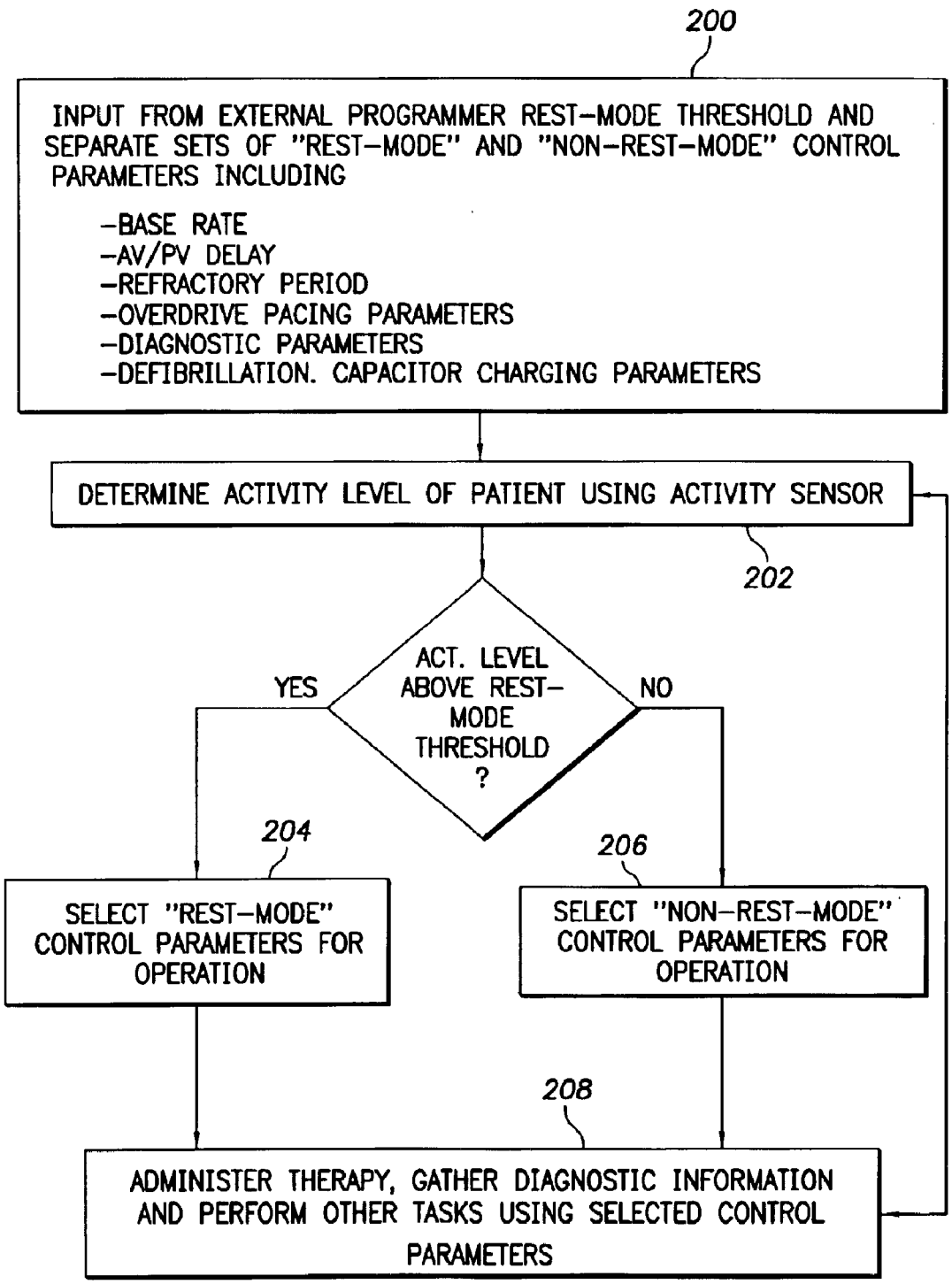
FIG. 4 is a flow chart providing an overview of the operation of a first embodiment of the invention wherein the implantable cardiac stimulation device of FIG. 2 selects a set of control parameters based on whether the patient is at rest.

Referring first to FIG. 4, a flow chart is shown describing an overview of the operation and novel features of cardiac stimulation device 10 as configured in accordance with the first embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the cardiac stimulation device. Those skilled in the art may readily write such a control program based on the flow charts and other descriptions presented herein.

Initially, at step 200, controller 60 (FIG. 2) inputs two sets of control parameters from an external programmer: a set of "rest-mode" control parameters selected by a physician for controlling the cardiac stimulation device while the patient is asleep (or otherwise at profound rest) and a set of "non-rest-mode" control parameters selected by the physician for controlling the cardiac stimulation device while the patient is awake (or otherwise not at profound rest). Dozens of control parameters may be specified in each set. Many of the control parameters will be the same for both the rest-mode and non-rest-mode sets. However, other parameters will be set differently by the physician so as to optimize operation of the cardiac stimulation device depending upon whether the patient is at rest. If the physician does not set specific parameters for rest-mode and non-rest mode, default parameters are employed. If the physician does not wish to have the cardiac stimulation device vary its operation based upon whether the patient is at rest, the physician controls the external programming to send appropriate signals to the cardiac stimulation device to disable separate rest-mode/non-rest-mode operation.

Examples of parameters that the physician may wish to set differently depending upon whether the patient is at rest include:
base pacing rate;
AV/PV delay;
refractory period;
overdrive pacing parameters;
diagnostic parameters; and
defibrillation capacitor charging parameters.

The base rate specifies a minimum rate at which the heart is paced. If the intrinsic rate falls below the base rate, the cardiac stimulation device thereby paces at the base rate. Typically, the base rate for rest-mode (also referred to as a rest rate) is considerably lower than the base rate for non-rest-mode. In one specific example, the non-rest mode base rate is set to 80 bpm, whereas the rest-mode base rate is 50 bpm. The AV/PV delay (or AV/PV interval) specifies a length of time between an atrial paced or sensed event and delivery of a ventricular pulse (if one is required). In the specific example, the non-rest mode AV/PV delay is set to 170 ppm/150 ppm, whereas the rest-mode AV/PV delay is set to 225 ppm/200 ppm. The refractory period specifies a timing cycle following a paced or sensed event during which time the sense amplifier will not respond to incoming signals. In the specific example, the non-rest mode refractory period is set to 250 ms, whereas the rest-mode refractory period is set to 325 ms.

The overdrive pacing parameters specify the manner by which overdrive pacing is to be performed. The following specific control parameters may be employed:

the number of overdrive events, i.e. the number of consecutive paced events which occur after overdrive pacing is triggered and before recovery begins.

the overdrive pacing response function (FIG. 3), which specifies the particular overdrive pacing rate to be applied at each detected heart rate when overdrive pacing is triggered.

the recovery rate, which specifies the rate decrement by which the pacing rate is decreased subsequent to initiation of overdrive pacing.

In the specific example, the non-rest mode overdrive pacing parameters specify response function #2 (FIG. 3), whereas the rest-mode overdrive pacing parameters specify response function #1 (FIG. 3) to thereby provide less aggressive overdrive pacing while the patient is at rest. The number of overdrive events and the refractory period may also differ to provide less aggressive overdrive pacing while the patient is at rest.

Diagnostic parameters specify the type of diagnostic data to be recorded and how often the data is to be recorded. Diagnostic data includes diagnostic information pertaining to the patient (patient data) such as internal electrocardiogram data (IEGM) and detection of various events such as premature atrial contractions (PACs) and premature atrial contractions (PVCs). Diagnostic data also includes diagnostic information pertaining to the cardiac stimulation device (device data) such as lead impedance, battery voltage, and the like. In the specific example, the rest-mode diagnostic parameters specify that certain types of device data are to be collected every hour, whereas the non-rest-mode diagnostic parameters specify that the device data is to be collected very fifteen minutes.

Defibrillation capacitor charging parameters are used by the device to determine whether to charge defibrillation capacitors of the device for possible delivery of a defibrillation pulse. The type and severity of any arrhythmia occurring in the patient is evaluated to determine whether to charge the capacitors. For example, if a mild tachycardia is detected, the capacitors are typically not charged. If a more severe tachycardia is detected, particularly a tachycardia of the type that may trigger fibrillation, the capacitors are charged in expectation of the need for a possible defibrillation pulse. In one implementation, the device continuously evaluates a risk of fibrillation and compares the risk to a programmed fibrillation risk threshold. The capacitors are charged whenever the risk exceeds the threshold. Some patients are more prone to fibrillation while asleep and so the risk threshold may be set to a lower value in rest-mode as compared to non-rest-mode.

Once the two sets of control parameters are input, the cardiac stimulation device begins to periodically determine the activity level of the patient at step 202, using the activity physiological sensor 108 (FIG. 2) preferably configured using the techniques described in the aforementioned patent to Bornzin et al. (U.S. Pat. No. 5,476,483). The activity level is compared with a predetermined rest-mode activity level threshold and, if it exceeds the threshold, the non-rest-mode control parameters are selected at step 204; otherwise, the rest-mode control parameters are selected at step 206. The activity level threshold may be provided by the physician along with the other control parameters or the activity level threshold may be preprogrammed into the cardiac stimulation device. In any case, at step 208, the controller controls the operation of the device in accordance with selected set of control parameters. Hence, therapy is administered, diagnostic data is collected, and other operations are performed using the set of control parameters appropriate to whether the patient is awake or asleep. Periodically, the controller returns to step 202 to update the activity level and, depending upon the updated activity level, the controller may then switch to the other set of control parameters. During a follow-up session, the physician may re-program the device causing the process to start over at step 200.

In this manner, the physician is able to program the operation of the implanted device to take into account whether the patient is awake or asleep (or otherwise at profound rest). If programmed using the specific exemplary parameters discussed above, then when the patient reaches a state of profound rest, the base rate is automatically lowered and overdrive pacing is made less aggressive to permit ease of sleep and to conserve battery power. Diagnostic data is collectedly less frequently to further conserve battery power. Parameters controlling charging of the defibrillation capacitors are set so that the capacitors are more readily charged to help compensate for any increased risk of fibrillation while the patient is asleep. When the patient awakes or otherwise begins to move around again, the base rate is automatically raised and overdrive pacing is made more aggressive. Diagnostic data is collectedly more frequently. Parameters controlling charging of the defibrillation capacitors are reset to a default state.

Figure 5:
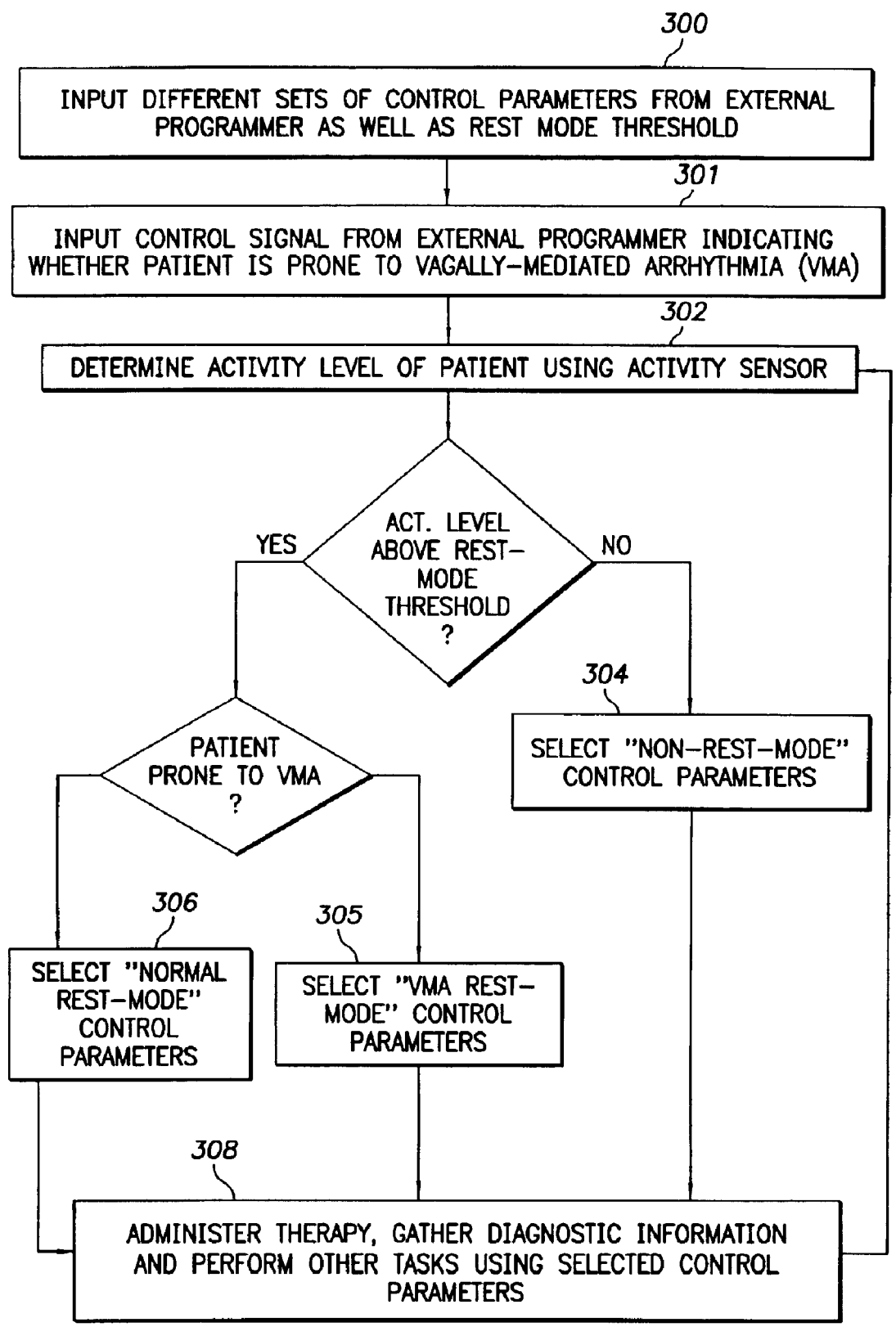
FIG. 5 is a flow chart providing an overview of the operation of a second embodiment of the invention similar to the first but wherein the implantable cardiac stimulation device of FIG. 2 also selects control parameters based on whether the patient is prone to vagally-mediated arrhythmias.

Referring now to FIG. 5, a method is described which further takes into account whether the patient is prone to vagally-mediated arrhythmias. Many of the steps of the method of FIG. 5 are similar to those of FIG. 4 and only pertinent differences will be described in detail. At step 300, the controller inputs three sets of control parameters from the external programmer specified by the physician: a set of "VMA rest-mode" control parameters for controlling the cardiac stimulation device while the patient is asleep if the patient is prone to vagally-mediated arrhythmias; a set of "normal rest-mode" control parameters for controlling the cardiac stimulation device while the patient is asleep if the patient is not prone to vagally-mediated arrhythmias; and a set of "non-rest-mode" control parameters for controlling the cardiac stimulation device while the patient is awake (or otherwise not at profound rest). Dozens of control parameters may be specified in each set--some will differ from set to set, others will not. Specific examples include the aforementioned base pacing rate, AV/PV delay, refractory period, overdrive pacing parameters, diagnostic parameters, and defibrillation capacitor charging parameters.

The non-rest-mode and normal rest-mode parameters may be set as described above with reference to FIG. 4 to generally provide for a lower base rate and less aggressive overdrive pacing while the patient is asleep and to generally provide for collection of less diagnostic data while the patient is asleep. However, the VMA rest-mode parameters are preferably set to provide for generally more aggressive overdrive pacing while the patient is asleep to thereby help compensate for an increased risk of arrhythmias occurring while the patient is asleep. For example, the VMA rest-mode parameters may specify overdrive pacing response function #3 (FIG. 3), rather than #1 or #2. The VMA rest-mode base rate is set to the same rate as the non-rest-mode base rate so that there is no reduction is base rate when the patient is asleep. Also, because a patient prone to vagally-mediated arrhythmias may be particularly at risk of fibrillation, the parameters pertaining to the charging of the defibrillation capacitor may be set so that the capacitor is automatically charged as soon as the patient falls asleep (or otherwise achieves a state of profound rest). The VMA rest-mode diagnostic parameters may specify that a greater amount of data be collected while the patient is asleep to aid in the subsequent diagnosis by the physician of any vagally-mediated arrhythmias.

Continuing with FIG. 5, once the three sets of control parameters are input at step 300, the cardiac stimulation device then inputs a signal at step 301 from the external programmer specifying whether the patient, in the opinion of the physician, is prone to vagally-mediated arrhythmias. Then, beginning at step 302, the cardiac stimulation device periodically determines the activity level of the patient and compares the activity level with a predetermined rest-mode activity level threshold. If the activity level exceeds the threshold, the non-rest-mode control parameters are selected at step 304. If the activity level does not exceed the threshold and the patient is prone is prone to vagally-mediated arrhythmias, the VMA rest-mode control parameters are selected at step 305. Otherwise, the normal rest-mode control parameters are selected at step 306. Thereafter, beginning at step 308, the controller controls the operation of the device in accordance with selected set of control parameters. Hence, therapy is administered, diagnostic data is collected, and other operations are performed using the set of control parameters appropriate to whether the patient is awake or asleep and appropriate to whether the patient is prone to vagally-mediated arrhythmias. Periodically, the controller returns to step 302 to update the activity level and, depending upon the updated activity level, the controller may then switch to the other set of control parameters. During a follow-up session, the physician may re-program the device causing the process to start over at step 300.

Figure 6:
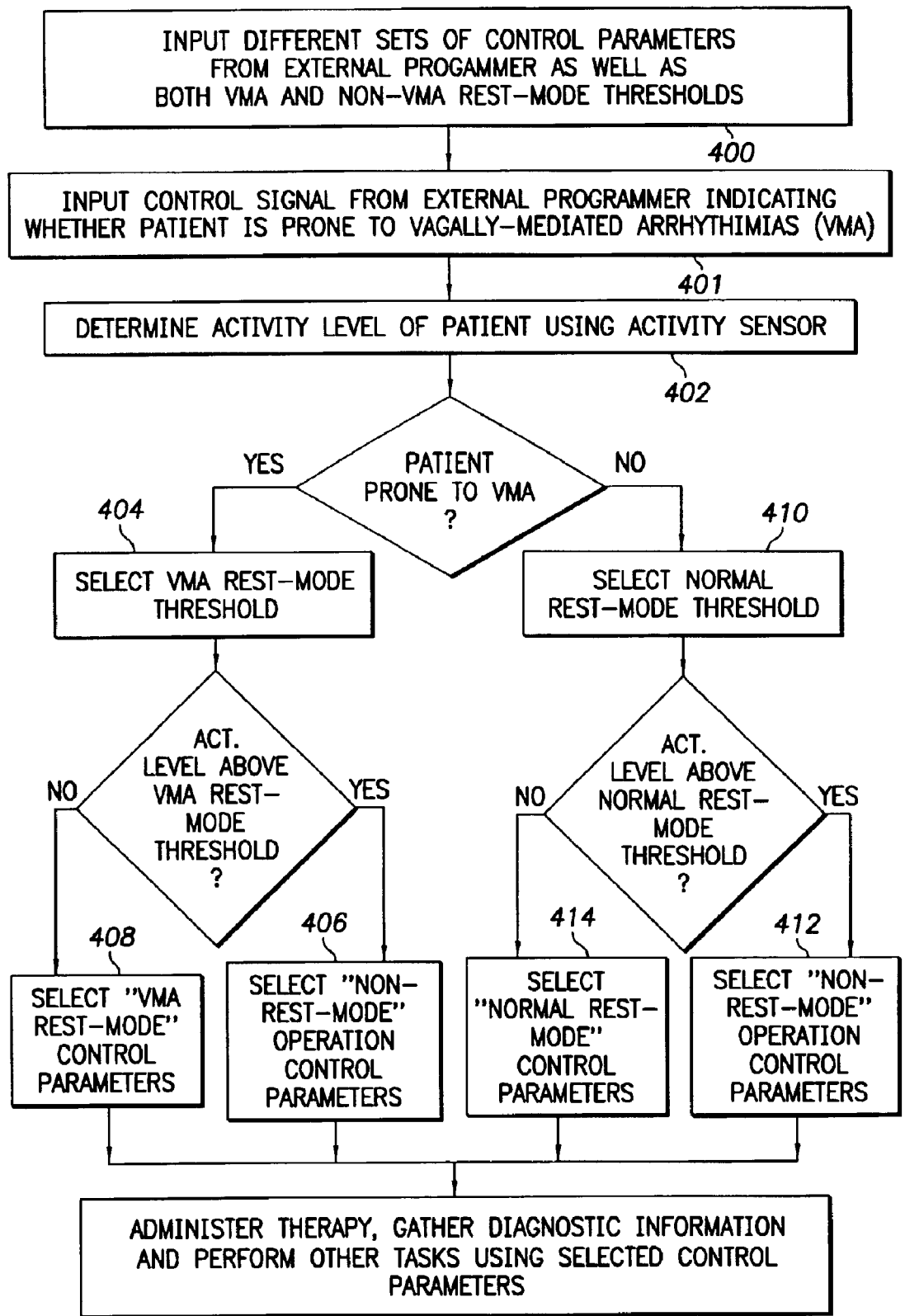
FIG. 6 is a flow chart providing an overview of the operation of a third embodiment of the invention wherein the implantable cardiac stimulation device of FIG. 2 selects a threshold for determining whether the patient is at rest based on whether the patient is prone to vagally-mediated arrhythmias.

Referring now to FIG. 6, a method is described which permits separate activity level thresholds to be specified depending on whether the patient is prone to vagally-mediated arrhythmias. Many of the steps of the method of FIG. 6 are similar to those of FIGS. 4 and 5 and only pertinent differences will be described in detail.

At step 400, the controller inputs three sets of control parameters from the external programmer specified by the physician: a set of "VMA rest-mode" control parameters for controlling the cardiac stimulation device while the patient is asleep if the patient is prone to vagally-mediated arrhythmias; a set of "normal rest-mode" control parameters for controlling the cardiac stimulation device while the patient is asleep if the patient is not prone to vagally-mediated arrhythmias; and a set of "non-rest-mode" control parameters for controlling the cardiac stimulation device while the patient is awake (or otherwise not at profound rest). As before, dozens of control parameters may be specified in each set. Specific examples include the aforementioned base pacing rate, AV/PV delay, refractory period, overdrive pacing parameters, diagnostic parameters, and defibrillation capacitor charging parameters.

The three sets of control parameters may be set by the physician as described above with reference to FIG. 5 to ensure that, if the prone to vagally-mediated arrhythmias, the most aggressive overdrive pacing is used while the patient is asleep. The sets of parameters also specify separate activity level thresholds which vary dependent on whether the patient is prone to vagally-mediated arrhythmias. The threshold for use with patients prone to vagally-mediated arrhythmias is referred to herein as the "VMA activity level threshold". The threshold for use with patients not prone to vagally-mediated arrhythmias is referred to herein as the normal activity level threshold. The VMA activity level threshold may be set, for example, lower than the normal activity level threshold so that, within patients prone to vagally-mediated arrhythmias, the cardiac stimulation device more readily switches to rest-mode to ensure that more aggressive overdrive pacing is promptly performed. For example, the normal threshold may be set such that a state of profound rest must be achieved for at least one half hour before the cardiac stimulation device switches to rest mode operation. However, the VMA threshold may be set such that the cardiac stimulation device switches to rest-mode operation even if only a lesser state of rest is achieved for a shorter period of time. In this manner, if the patient is prone to vagally-mediated arrhythmias, aggressive overdrive pacing is initiated promptly as the patient begins to fall asleep.

Once the three sets of control parameters are input at step 400, the cardiac stimulation device then inputs a signal at step 401 from the external programmer specifying whether the patient is prone to vagally-mediated arrhythmias. At step 402, the cardiac stimulation device determines the activity level of the patient. If the patient is prone to vagally-mediated arrhythmias, then the cardiac stimulation device compares the activity level with the VMA rest-mode activity level threshold at step 404. If the activity level exceeds the VMA threshold, the non-rest-mode control parameters are selected at step 406; otherwise, the VMA rest-mode control parameters are selected at step 408. On the other hand, if the patient is not prone to vagally-mediated arrhythmias, then the cardiac stimulation device compares the activity level with the normal rest-mode activity level threshold at step 410. If the activity level exceeds the normal threshold, the non-rest-mode control parameters are selected at step 412; otherwise, the normal rest-mode control parameters are selected at step 414. Thereafter, beginning at step 416, the controller controls the operation of the device in accordance with selected set of control parameters. Periodically, the controller returns to step 402 to update the activity level and, depending upon the updated activity level, the controller may then switch the set of control parameters. During a follow-up session, the physician may re-program the device causing the process to start over at step 400.

Thus FIG. 6 illustrates an implementation which provides three separate sets of control parameters (normal rest-mode, VMA rest-mode and non-rest-mode) and which further permits the activity level threshold to be set based on whether the patient is prone to vagally-mediated arrhythmias. In other implementations, four separate sets of control parameters are provided (normal rest-mode, VMA rest-mode, normal non-rest-mode, and VMA non-rest-mode). The implementations using four separate sets of control parameters may also exploit the separate activity level thresholds are may be configured to use only a single activity level threshold. In still other implementations, the separate activity level thresholds are used with only two sets of control parameters (normal rest-mode and normal non-rest-mode). As can be appreciated, a wide range of implementation are provided by the invention and no attempt is made herein to enumerate all possible implementation.

What have been described are various techniques for selecting sets of control parameters for use within implantable cardiac stimulation devices. Although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device for implant within a patient having a controller for controlling functions of the cardiac stimulation device, a method comprising the steps of:
   detecting whether a patient in which the cardiac stimulation device is implanted is prone to vagally-mediated arrhythmias;
   controlling the functions of the cardiac stimulation device using the controller based on whether the patient is prone to vagally-mediated arrhythmias;
   determining whether the patient is at rest and wherein the step of controlling the functions of the cardiac stimulation device using the controller is further based on whether the patient is at rest.

2. The method of claim 1 wherein the implantable cardiac stimulation device also includes a telemetry device for inputting signals for use in controlling operation of the controller and wherein the step of detecting whether the patient is prone to vagally-mediated arrhythmias is performed by inputting a control signal using the telemetry device indicative of whether the patient is prone to vagally-mediated arrhythmias.

3. The method of claim 1 wherein the implantable cardiac stimulation device includes an activity sensor providing a signal indicative of a level of activity of the patient and wherein the step of determining whether the patient is at rest is performed by comparing the activity level to a predetermined rest-mode triggering level.

4. The method of claim 1 wherein if the patient is prone to vagally-mediated arrhythmias, a predetermined rest-mode triggering level is set higher than if the patient is not prone to vagally-mediated arrhythmias.

5. The method of claim 1 wherein if the patient is prone to vagally-mediated arrhythmias, selected functions of the implantable cardiac stimulation device are controlled using a first set of parameters while at the patient is at rest and using a second set of parameters while not at rest.

6. The method of claim 5 wherein the selected functions include overdrive pacing and wherein the first set of parameters used for a patient prone to vagally-mediated arrhythmias while the patient is at rest provides generally more aggressive overdrive pacing than the second set of parameters used while the patient is not at rest.

7. The method of claim 6 wherein the first and second sets of parameters specify overdrive pacing response functions for use in overdrive pacing the heart and wherein the overdrive pacing function of the first set of parameters provides a generally higher overdrive pacing rate than the overdrive pacing function of the second set of parameters.

8. The method of claim 6 wherein the first and second sets of parameters specify overdrive pacing recovery rates for use in overdrive pacing the heart and wherein the overdrive pacing function of the first set of parameters provides a generally slower overdrive pacing recovery rate than the overdrive pacing recovery rate of the second set of parameters.

9. The method of claim 6 wherein the first and second sets of parameters specify a number of overdrive beats to be paced at an overdrive rate before any recovery begins and wherein the number of overdrive beats of the first set of parameters is greater than the number of overdrive beats of the second set of parameters.

10. The method of claim 5 wherein the selected functions include periodic diagnostic information gathering and wherein the first set of parameters used for a patient prone to vagally-mediated arrhythmias while the patient is at rest provides for more frequent diagnostic information gathering than the second set of parameters used while the patient is not at rest.

11. The method of claim 5 wherein the selected functions include diagnostic information gathering and wherein the first set of parameters used for a patient prone to vagally-mediated arrhythmias while the patient is at rest provides for gathering of additional diagnostic information than provided by the second set of parameters used while the patient is not at rest.

12. The method of claim 5 wherein the selected functions include base rate pacing and wherein the first set of parameters used for a patient prone to vagally-mediated arrhythmias while the patient is at rest provides a base pacing rate at least as high as a base rate of the second set of parameters used while the patient is not at rest.

13. The method of claim 5 wherein if the patient is not prone to vagally-mediated arrhythmias, selected functions of the implantable cardiac stimulation device are controlled using the second set of parameters regardless of whether the patient is at rest.

14. An implantable cardiac stimulation device for implant within a patient comprising:
   control means for controlling selected functions of the device;
   storage means for storing sets of control parameters for use by the control means, the storage means storing a first set of control parameters for use if the patient is prone to vagally-mediate arrhythmias and a second set of control parameters for use if the patient is not prone to vagally-mediate arrhythmias; and
   means for detecting whether the patient is prone to vagally-mediated arrhythmias; and
   wherein the controller means inputs the first set of control parameters from the storage means if the patient is prone to vagally-mediated arrhythmias for use in controlling the selected functions of the devices and inputs the second set of control parameters from the storage means if the patient is not prone to vagally-mediated arrhythmias for use in controlling the selected functions of the device; and
   wherein the selected functions include overdrive pacing and wherein the first set of control parameters used for a patient prone to vagally-mediated arrhythmias while the patient is at rest provides a more aggressive overdrive pacing than the second set of control parameters used while the patient is not at rest.

15. The device of claim 14 wherein the first and second sets of parameters specify overdrive response functions for use in overdrive pacing the heart and wherein the overdrive pacing function of the first set of parameters provides a higher overdrive pacing rate than the overdrive pacing function of the second set of parameters.

16. The device of claim 14 wherein the first and second sets of parameters specify overdrive pacing recovery rates for use in overdrive pacing the heart and wherein the overdrive pacing function of the first set of parameters provides a slower overdrive pacing recovery rate than the overdrive pacing recovery rate of the second set of parameters.

17. The device of claim 14 wherein the first and second sets of parameters specify a number of overdrive beats to be paced at an overdrive rate before any recovery begins and wherein the number of overdrive beats of the first set of parameters is greater than the number of overdrive beats of the second set of parameters.

18. An implantable cardiac stimulation device for implant within a patient comprising:
- a pulse generator that generates pacing pulses for applying to the heart of a patient;
- a detector that detects whether the patient is prone to vagally-mediated arrhythmias; and
- a controller that controls the pulse generator of the device based on
- whether the patient is prone to vagally-mediated arrhythmias;
- wherein the controller overdrive paces the heart more aggressively when the patient is prone to vagally-mediated arrhythmias than when the patient is not prone to vagally-mediated arrhythmias.

19. The device of claim 18 wherein an overdrive pacing rate is higher when the patient is prone patient is prone to vagally-mediated arrhythmias than when the patient is not prone to vagally-mediated arrhythmias.

20. The device of claim 18 wherein an overdrive pacing recovery rate is slower when the patient is prone to vagally-mediated arrhythmias than when the patient is not prone to vagally-mediated arrhythmias.

21. The device of claim 18 wherein the controller specifies a number of overdrive beats to be paced at an overdrive rate before recovery begins and wherein the number of overdrive beats is greater when the patient is prone to vagally-mediated arrhythmias than when the patient is not prone to vagally-mediated arrhythmias.

* * * * *